United States Patent [19]

Baskas

[11] Patent Number: 5,035,703

[45] Date of Patent: Jul. 30, 1991

[54] DISPOSABLE SYRINGE NEEDLE AND SCALPEL HOLDER

[76] Inventor: Morris J. Baskas, 200 California Rd. #14, Bronxville, N.Y. 10708

[21] Appl. No.: 595,238

[22] Filed: Oct. 10, 1990

Related U.S. Application Data

[63] Continuation-in-part of Ser. No. 520,733, May 9, 1990, Pat. No. 4,995,870.

[51] Int. Cl.⁵ ............................................. A61M 5/32
[52] U.S. Cl. ................................... 606/167; 604/192
[58] Field of Search ................ 604/110, 192; 606/167, 606/182; 30/329, 342, 335; 206/363, 366

[56] References Cited

U.S. PATENT DOCUMENTS

| 3,176,395 | 4/1965 | Warner et al. ................. 30/329 X |
| 4,823,457 | 4/1989 | Prochaska ............................ 30/342 |
| 4,936,014 | 6/1990 | Shaanan et al. ................. 30/329 X |

FOREIGN PATENT DOCUMENTS

| 9000414 | 1/1990 | World Int. Prop. O. .......... 604/110 |
| 9000070 | 11/1990 | World Int. Prop. O. .......... 604/110 |

*Primary Examiner*—John D. Yasko

[57] ABSTRACT

A holder for a used needle removed from a hypodermic syringe or a used scalpel blade. The holder safely encloses the needle or blade, and can be safely disposed of with the needle or blade. The holder is supported on a base with a releasable fitting enabling the holder to be oriented at assorted angles. The holder can also serve to support the syringe or scalpel while treating a patient.

8 Claims, 8 Drawing Sheets

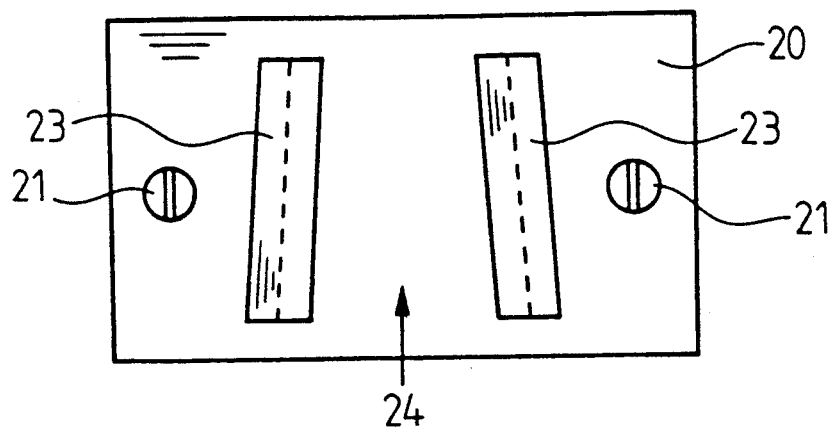
Figure 2.
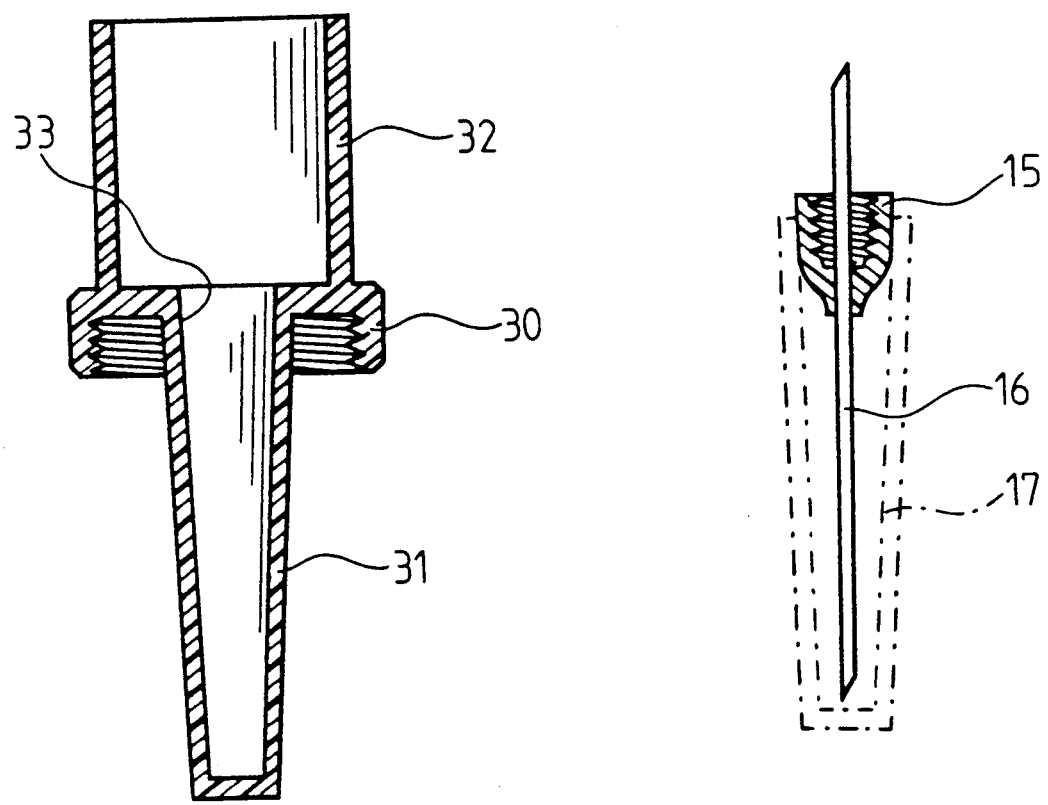
Figure 3.
Figure 4.

DISPOSABLE SYRINGE NEEDLE AND SCALPEL HOLDER

RELATED APPLICATION

This application is a continuation-in-part of my earlier filed patent application, Ser. No. 520,733, filed May 9, 1990 now U.S. Pat. No. 4,995,870.

BACKGROUND OF THE INVENTION

This invention relates to a disposable device for used syringe needles and scalpel blades, and can allow function as a holder for such devices.

In my prior application, whose contents are hereby incorporated by reference, I describe a holder for use with a hypodermic syringe to assist a user in assembling and disassembling the syringe. In the embodiments described in that application, a card or spring-loaded clips is used to hold the conventional sheath which houses the needle. Also, the card can be provided with adhesive bands so it can be folded over the used needle to cover and protect same against accidental contact by another person.

SUMMARY OF THE INVENTION

The present invention has an object an improved holder for a syringe needle, in which at least part of the holder encloses and protects against accidental contact with the needle.

Another object of the invention is an improved holder which affords easy disposal of a used needle.

Still another object of the invention is a disposable holder for used needles and scalpel blades which can also serve to support the syringe or scalpel for repeated use on the same patient.

These and further objects and advantages of the invention are achieved, in accordance with one aspect of the invention, by a holder having a first hollow member which at one end is sized to releasably grip the hub of a disposable needle. The working forward end of the needle is safely confined within the hollow member. Above the gripping end is provided a second hollow member sized to receive the syringe and surround and protect the rearward needle end when separated from the syringe barrel.

The practitioner can at any time insert the syringe into the first hollow member, where it will be safely held by the second hollow member. When the practitioner desires, the syringe barrel is readily detached from the needle hub, leaving the separated needle lodged safely in the holder first hollow member. The latter can then be safely disposed of.

In a preferred embodiment, means are provided on the holder, or on a base support for the holder, that allows the holder to be oriented in several different positions for the convenience of the practitioner.

In accordance with another aspect of the invention, a similarly configured holder or stand is adapted to support a scalpel while in use. Following use, the scalpel blade can be detached from its handle and lodged safely in the holder for safe disposal.

Another aspect of the invention is a novel support for the holder which allows orientation in multiple positions for the user's convenience.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

FIG. 2 is a plan view of a base support for the holder of FIG. 1;

FIGS. 3 and 4 show, respectively, the hollow member of the first embodiment, and a typical disposable needle with its protective sheath;

DETAILED DESCRIPTION OF THE PREFERRED EMBODIMENTS

Figure 1:
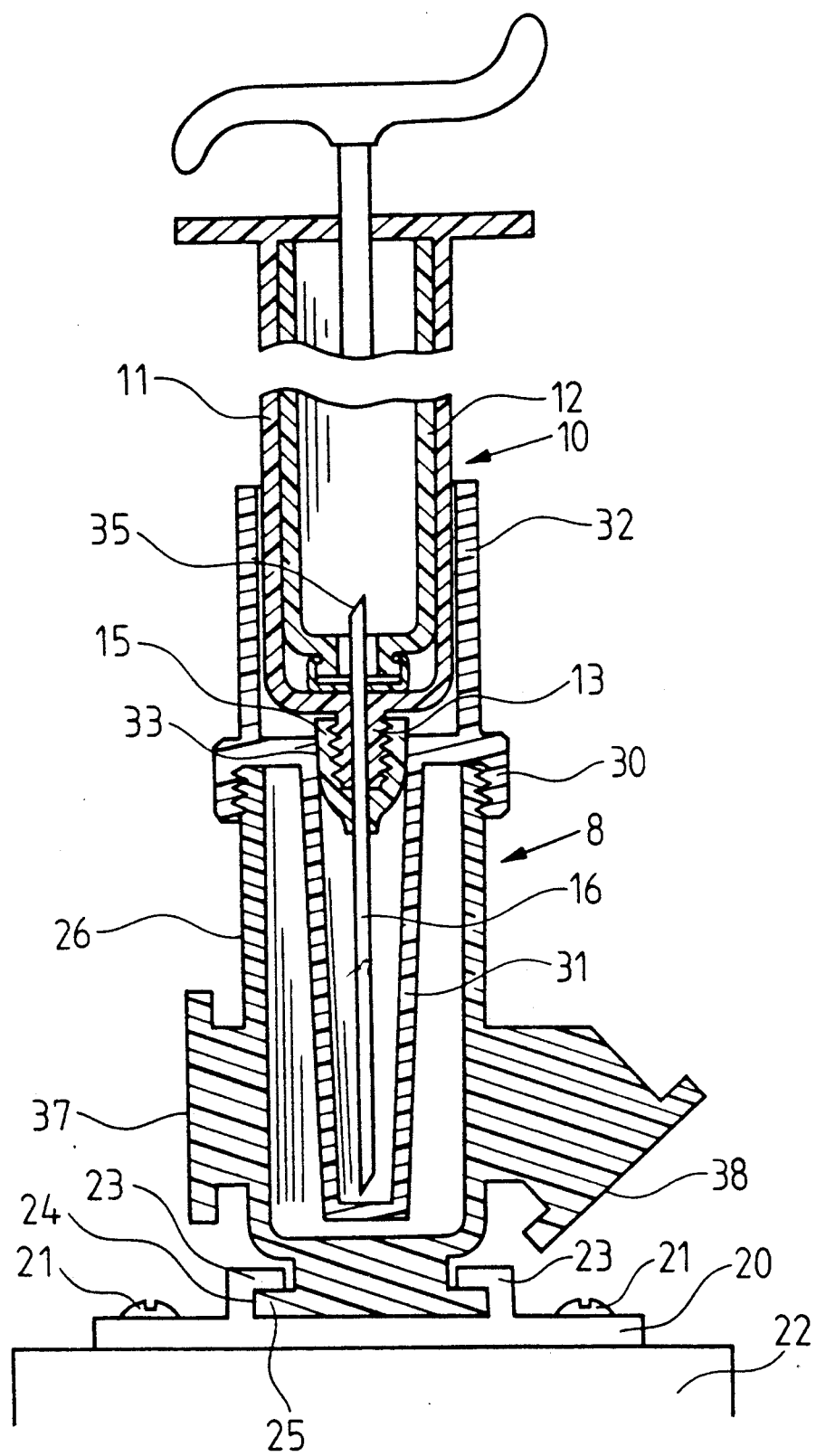
FIG. 1 is a vertical cross-section of one form of holder in accordance with the invention, showing a syringe being supported thereby.

FIG. 1 illustrates one form of device 8 in accordance with the invention, shown for use with a standard dental syringe 10 of the type comprising a metal barrel 11 for receiving a cartridge 12 with medication. The usual plunger is not shown. The barrel bottom terminates in a hollow threaded end 13 for receiving the threaded hub 15 supporting a conventional disposable needle 16. The needle when separated is shown in FIG. 4, with the bottom housed in a removable protective cap or sheath 17. When the needle hub 15 is screwed onto the syringe end 13, the needle back end penetrates a diaphragm at the cartridge bottom and enters the medication stored in the cartridge 12.

The device 8 of the invention comprises a base member 20 having means, for example, the screw fasteners 21, for mounting the base 20 to any suitable table top or side 22. Projecting upward from the base 20 are flanged members 23 which gradually taper inward toward one another as illustrated in the top view of FIG. 2. The flanged members 23 form a tapered slot-shaped receptacle 24 for removably receiving and anchoring a T-shaped mating member 25 at the bottom of a stand 26. By sliding the T-end 25 into the slot 24 from the front until the T-edges engage the flange walls, the stand 26 can be anchored to the base 20, yet be easily removed by reversing the movement.

The stand 26 is closed off on top by a threaded cap 30 having, depending below the cap, a closed sheath 31 corresponding to the first hollow member, and projecting upwards a cylindrical open-end element 32 corresponding to the second hollow member, termed herein a chimney. The sheath 31 has a gripping opening 33 whose diameter is substantially equal to that of the hub 15. The sheath 31, as will be noted, tapers gradually inwardly.

The configuration is such that when the needle hub 15 is pushed downward into that sheath opening 33, a snug fit results. The hub is typically of plastic, and the stand and cap are also made of plastic material, so that when the hub is inserted, it is held in the opening 33 and sufficiently gripped such that the syringe 10 can be screwed and unscrewed from the hub 15, yet if desired, when the syringe is pulled by the practitioner, the syringe 10 plus the attached hub 15 with needle 16 can be separated from the cap 30. The spacing between the syringe wall 11 and the inner side of the chimney 32 is such that the syringe is easily inserted into the chimney, yet the syringe will be supported in an upright position.

When used by a dental practitioner, the base 20 is conveniently mounted on a table. The dentist inserts the stand 26 into the channel 24. The dentist then inserts the cartridge 12 into the syringe, removes the upper cover of a disposable needle, and holding the protective cover 17 then screws the hub 15 onto the threaded part 13. He then can use the syringe to inject medication into the patient. He can then insert the syringe 10 into the chimney 32 until the hub 15 engages the opening 33. The syringe when released will be supported in a sterile condition within the sheath 31, assuming the latter is part of a fresh, unused cap sub-assembly 30. If desired, the syringe can be removed and further medicament injections given to the same patient, each time returning the syringe to the stand holder. When the procedure is completed, and the syringe returned to the holder, the dentist rotates the syringe 10 to unscrew it from the hub 15, and removes the syringe 10, the hub 15 with attached needle 16 remaining behind safely protected inside the cap 30. The front used needle end remains at all times within the sheath 31. The height and diameter of the chimney 32 is chosen such that the rear top, referenced 35, of the needle remains sufficiently below the chimney top that the finger of the dentist or an assistant if accidentally pushed into the chimney will not touch the needle tip 35. A chimney height of about seven-eighths inches, and a chimney ID of about one-half inches is suitable for this purpose. The dentist can then unscrew the cap 30 with the enclosed needle from the stand, and dispose of it. Thus, the used needle is never touched prior to, during, or after use on the patient. Moreover, in the disposed condition, the used needle end, which entered the patient, remains at all times within the protective sheath 31. The dentist then places a fresh cap 30 on the stand 26, and is prepared for the next patient.

Figure 5:
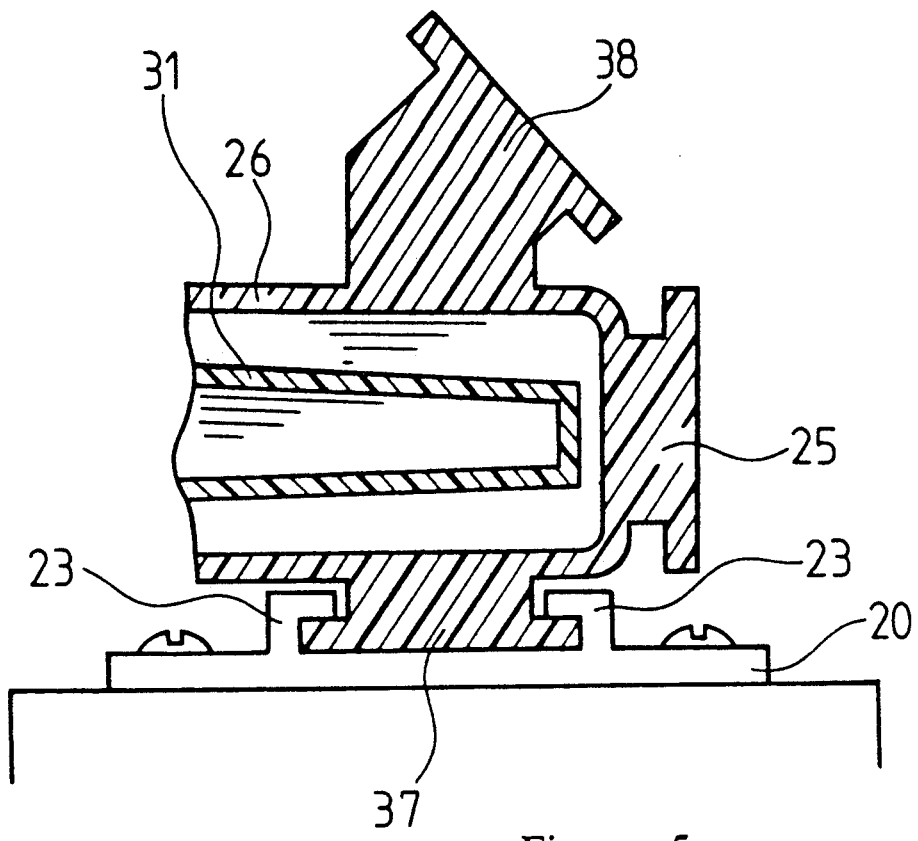
FIGS. 5 and 6 are partial views of the holder of FIG. 1 shown in two different orientations.
Figure 6:
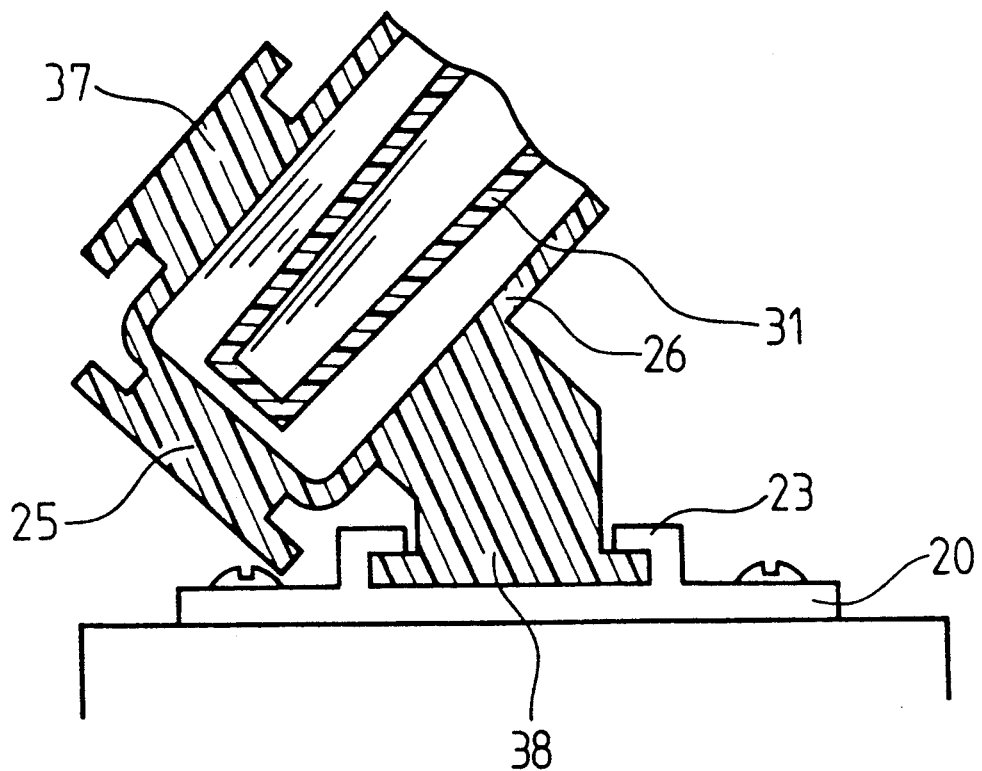

As will be observed, the stand contains two additional T-shaped fittings 37, 38. The fitting 37 on the left is used when the dentist desires to mount the stand 26 horizontally as shown in FIG. 5, or vertically when the base 20 is mounted on a vertical wall. The fitting 38 is used when the dentist desires to have the stand 26 project at a 45° angle, as shown in FIG. 6. Thus, with respect to the T-fitting 25, the T-fitting 37 is rotated 90°, and the T-fitting 38 is rotated 45°. Other angles can be chosen if desired. It will also be appreciated that other ways of releasably securing the cap to the stand can be substituted for the threaded engagement illustrated.

Figure 7:
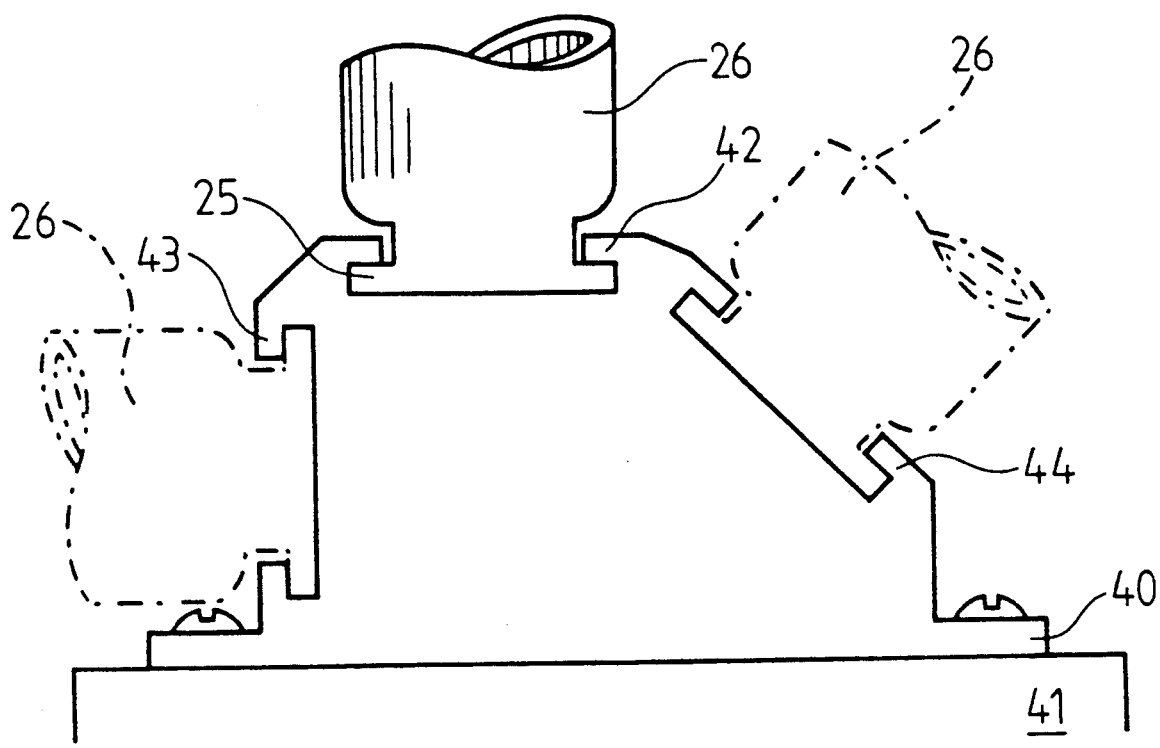
FIG. 7 is a partial view of a modification of the holder of FIG. 1.

In the embodiment so far described, multiple fittings 25, 37, 38 are provided on the stand 26 for selective engagement with one mating fitting 24 on the base 20, to afford the dentist the versatility of mounting the stand at a selected orientation as he prefers. Alternatively, the stand can be provided with a single T-fitting for mating with one of variously oriented slots on the base. This modification, which is preferred, is illustrated in FIG. 7. A base member 40 is mounted, as by screws or other suitable fasteners or adhesives, to a workbench 41. The base 40 is provided with three flanged fittings 42, 43, 44 mounted horizontally, vertically, and at a 45° angle, respectively. The stand 26 is shown with its T-fitting 25 mounted in the flanged slot 42, so as to extend vertically similarly to the position shown in FIG. 1. For a horizontal orientation, the stand 26 can be mounted as shown in phantom in the flanged slot 43, or to extend at a 45° angle in the flanged slot 44.

Figure 8:
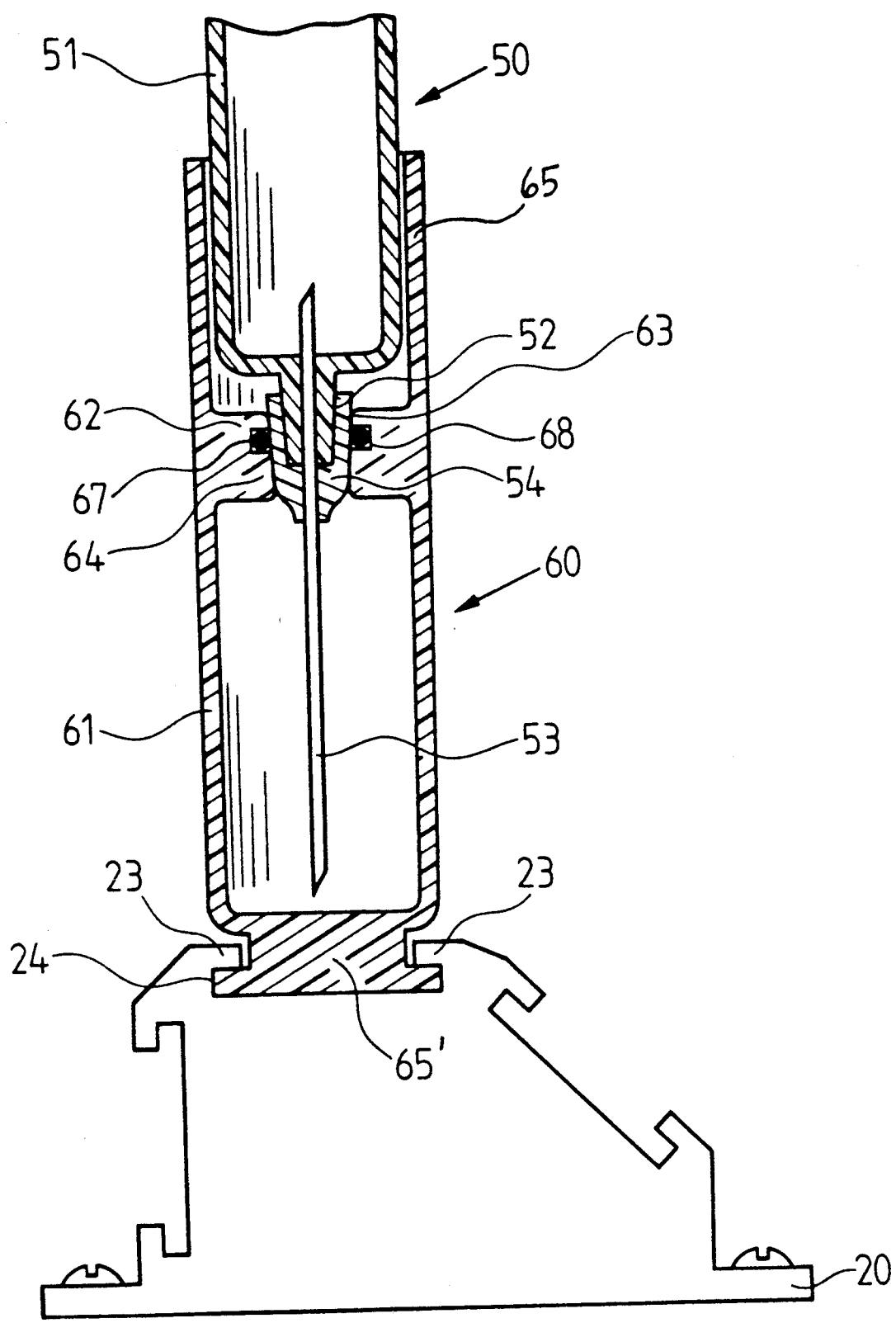
FIG. 8 is a view similar to FIG. 1 of a further modification especially suitable for plastic syringes.

In the embodiments so far described, which is especially suited for dental syringes with threaded hubs, the cap with enclosed used needle is discarded after use, but the stand remains behind for further use. In the next embodiment, there is no removable cap, and the entire stand is disposed of when the procedure is completed. This is illustrated in FIG. 8, and is best suited for the one time disposable plastic syringes commonly used by medical practitioners. These type of syringes, designated 50, typically comprises a plastic syringe body 51 with a non-threaded stem 52 adapted to receive a disposable needle 53 containing a non-threaded hub 54. The stem and hub come in standard sizes such that when the hub 54 is pushed onto the stem 52, it is held by a friction fit, and the barrel can then be filled with a desired medicament and injected into the patient.

In this embodiment, the stand 60 comprises a one-piece plastic molded member comprising an enclosure 61 corresponding to the first hollow member with an inner projecting wall 62 forming a hub-receiving gripping opening 63 inside a tapered spout 64. A chimney extension 65 corresponding to the second hollow member projects upwardly as before.

The operation is similar to that of the previous embodiments. The stand 60 is slid into the slot 24 to hold same upright. The used syringe 50 is then inserted into the chimney until the needle hub 54 snugly engages the opening 63 in the spout 64. The syringe body 51 can then be twisted to separate it from the needle hub 54, removed and discarded, the needle being captured by the stand opening 63 and remaining behind. The rear needle end, as before, remains protected within the chimney 65. The dentist then removes the entire stand from its base support 20 and discards the entire stand with the used needle fully enclosed and protected. To reduce costs, it is preferred that the disposable stand 60 contains a single mounting fitting 65, and, if multiple orientations are desired, that the base 40 shown in FIG. 7 is employed. Alternatively, a base with a single T-slot can be employed, but assorted bases with T-slots at assorted orientations can be made available to suit a particular user's preference.

As will be observed, the device of FIG. 8, being smaller and made of one-piece, will require less material and thus will be less expensive to fabricate, and therefore less costly to dispose of. Since medical practitioners often employ syringes of various sizes, it is a relatively simple matter to provide the practitioner with an assortment of such stands each configured for use with a particular sized syringe but mountable on the same base 20.

The slight tapering of the spout 64 forming the hub-receiving opening 63 will accommodate hubs 54 whose ODs slightly differ. If desired, to increase the frictional holding force, an O-ring 67 of rubber or plastic can be mounted in a slot 68 within the spout opening 63, as shown in FIG. 8.

It will be appreciated that various other forms of fittings can be used for removably attaching the stand to its base, as well as for holding the cap onto the stand in the FIG. 1 embodiment. While the T-shaped fitting with the tapered slot is preferred, because it locks the stand against rotation allowing one-handed use, the invention is not limited to such an attachment.

Figure 9:
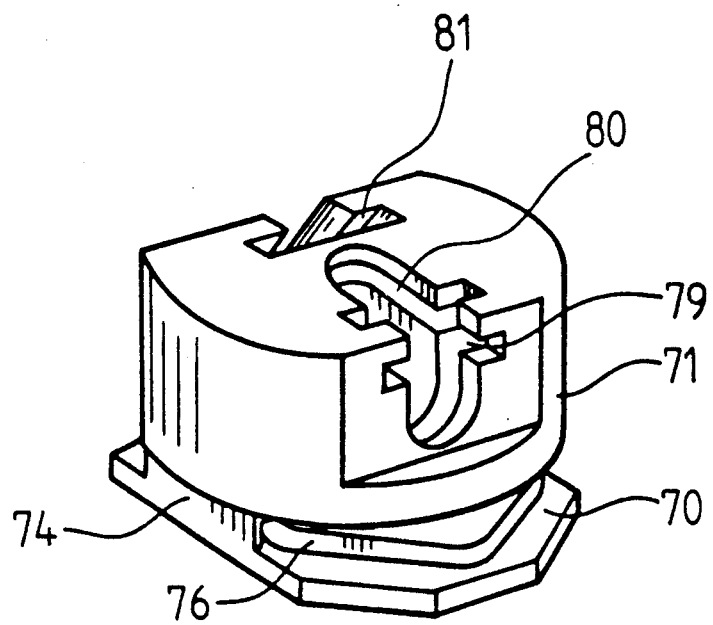
FIG. 9 is a perspective view of a modification of the holder base.
Figure 10:
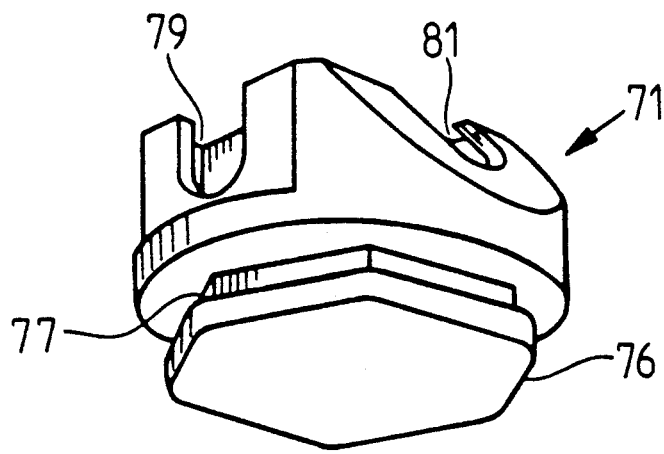
FIGS. 10 and 11 are perspective views of the two parts of the base of FIG. 9.
Figure 11:
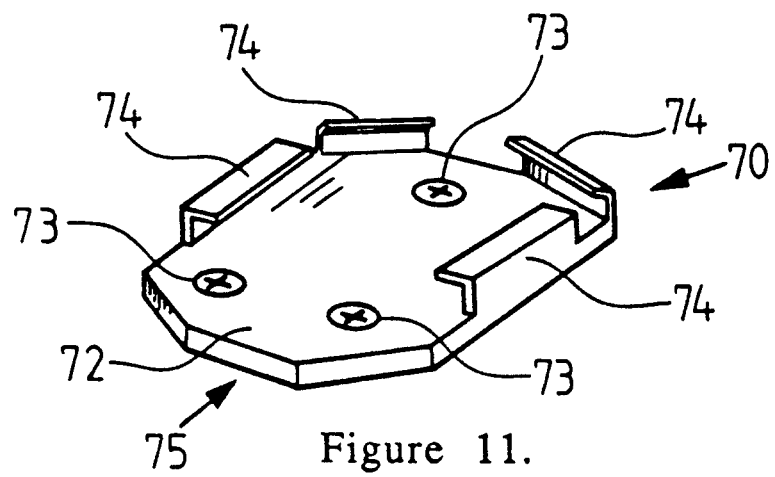
Figure 12:
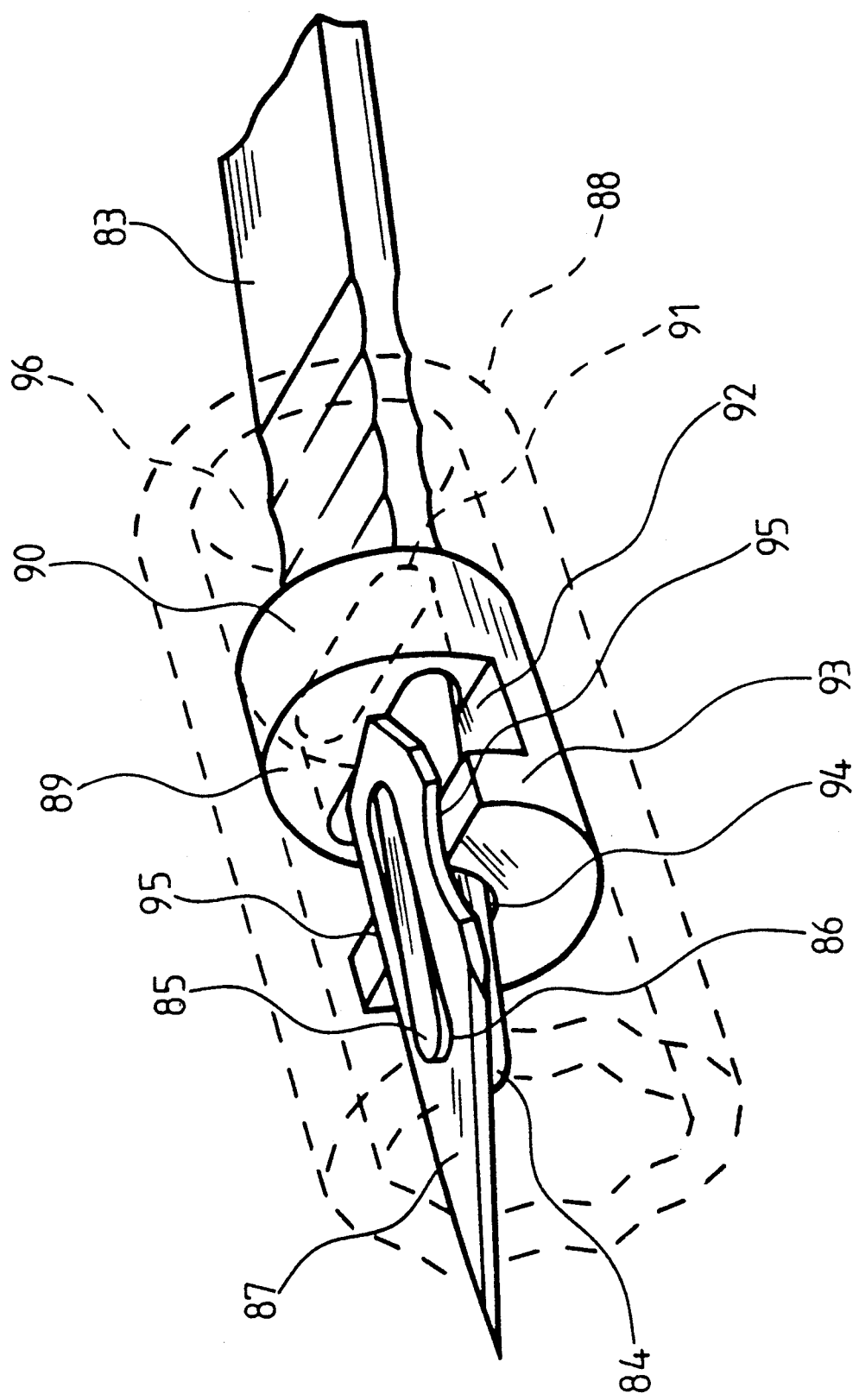
FIG. 12 is a perspective view of a modified holder for a scalpel.

FIG. 9 illustrates a modified fitting for supporting a stand of the type previously described as well as a stand suitable for a scalpel, described below. In this embodiment, the fitting comprises two parts 70, 71. The lower part 70 is a flat plate 72 having mounting holes for receiving screws 73 (FIG. 11) for mounting horizontally or vertically on a support surface. Four raised flanged elements 74 arranged on three sides provide a receptacle for removably receiving from the fourth side 75 a hexagonal base 76 on the upper part 71 (FIG. 12). The hexagonal base allows the upper part 71 to be rotated into any one of six possible rotary positions and then inserted and detachably held on the plate 70. A recessed hexagonal area 77 is gripped by the flanged ends of the elements 74. The upper part 71, similarly to the base member 40 of FIG. 7, contains multiple slots for receiving the grooved base of the stand 26. FIG. 9, which shows the upper part 71 assembled to the plate 70 in one of its six positions, illustrates a vertically oriented slot 79 for supporting a horizontal stand, a horizontally-oriented slot 80 for supporting a vertical stand, and a tilted slot 81 for supporting a tilted stand. The multiple-oriented slots and the multiply-positionable part 71 combine to allow positioning of the stand for the user's convenience in a multitude of positions. Other slots can be placed on other surfaces of the part 71 to add to the possibilities. It will be evident that the modified base of FIGS. 9-11 provides a very versatile support for the disposable stand or holder. It is also usable with a scalpel holder now described.

In the previous embodiments, the stand was used to support a syringe and for safe disposal of a used needle. A similar construction can be used for similar purposes for a conventional scalpel with a detachable conventional blade. This is illustrated in FIG. 12, with the scalpel handle shown at 83 having a lower shank portion 84 containing a raised ridge 85 adapted to engage a slot 86 in a standard disposable blade 87. A stand 88, shown in phantom, is of the type illustrated at 60 in FIG. 8 with a single T-shaped bottom portion at its left for use with the base of FIGS. 9-11. The stand interior is different, however. A single plastic piece 89, generally cylindrical, is wedged or glued inside the cylindrical stand 88. It comprises an upper cylindrical part 90 with a slot 91 for passage of the scalpel. A cut-out section 92 separates the part 90 from a semi-circular lower part 93 having a hole 94 for passage of the scalpel shank 84. The hole 94 defines two shoulders 95 on which the blade edges bordering the slot 86 rest. The alignment of the slot 91 with the hole 94 is slightly off center, so that when the scalpel is inserted through the top open end 96 of the stand, the handle 83 is slightly tilted as shown about 10° off of the axis of the cylindrical stand 88.

The stand will support the scalpel in a safe position with the blade mounted and protected (the bottom left end, not shown, of the stand 88 is closed off) and can be repeatedly inserted and removed by the user. When, however, the scalpel handle is pushed further inward to the position shown in FIG. 12, the slightly angled motion (to the left in FIG. 12) causes the shoulders 95 to cam the blade back end up and over the ridge 85, which loosens the blade 87. Now, if the user withdraws the handle 83, the bottom portion of part 90 detaches the blade 87 which then remains safely behind protected inside the stand 88. The latter with the used blade can then be safely disposed of.

The same stand can also be used to receive used suture needles, which will fall through the part 89 to the bottom, after which it can be used to remove the scalpel blade. The base in FIGS. 9-11 will also support two individual stands if needed by the user.

Figure 13:
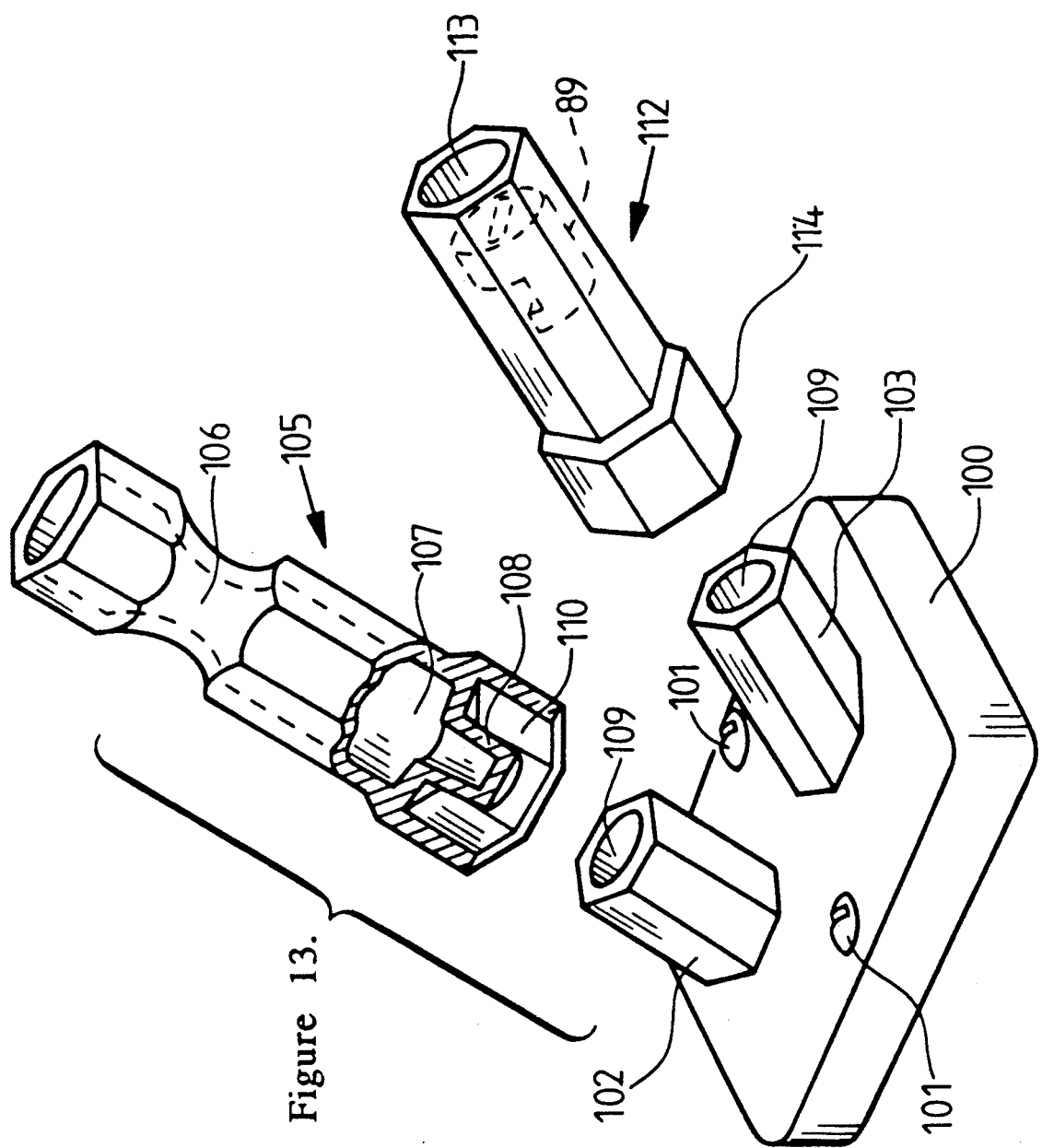
FIG. 13 shows a further modification.

FIG. 13 shows a further modification providing adjacent stands for say a scalpel and a syringe. A base 100 has provision for screw 101 mounting. Alternatively, a layer of contact cement can be provided on the bottom or side surfaces. Upstanding from the base 100 are two hexagonal hollow members 102,103, with one 102 oriented at for instance 60° and the other 103 at 45°. These are designed to receive and support a syringe or scalpel stand. A syringe stand 105 is shown at the left, and is of the type illustrated in FIG. 8 except that the outer configuration is hexagonal and the bottom portion is different. Otherwise the stand 105 comprises a hollow member with a restricted portion 106 sized to grip the hub of a syringe, as in FIG. 8, to allow removal of the needle, which is retained in a closed area 107 having at its bottom a closed nipple 108 sized to fit within the opening 109 in the member 102 when the stand 105 is placed over the member 102 and pushed down to seat on it. A cavity 110 in the stand bottom fits over the member 102 and holds the former in an upright position. With the parts made of plastic, for example, polypropylene, a little resiliency is present to provide a safe but removable connection of the stand for ultimate disposal of the contained used needle. The complementary hexagonal surfaces help to prevent rotation of the stand when the user rotates the syringe. The cavity 110 can also be cylindrical. The depending nipple 108 allows for safe storage of the detached needle. The hole 109 allows for a short stand but with an elongated protected region—the nipple 108—which can receive the latter.

The members 102,103 are preferably at different angles so as to prevent interference between adjacent instruments. A stand 112 on the right is of the type illustrated in FIG. 12 for holding a scalpel and for blade removal. It contains on the inside a member 89 corresponding to the member 89 of FIG. 12. An opening 113 on top is to receive the scalpel. The bottom portion 114 is configured similarly to that of the stand 105 and operates the same way. It can be fitted over and supported on either of the members 102, 103.

Alternatively, a pin can be mounted in the stand, transverse to the stand axis, which passes through the part 89 and whose inner end is opposite the blade rear end. When the pin is pushed inward by the user, the inner end pushes the blade rear off the ridge to detach the blade.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A device for assisting in safely demounting of a blade having a slotted rear end from a scalpel handle comprising:

a hollow member for receiving and holding the scalpel when the blade end is inserted, means connected to the hollow member for detaching the scalpel blade from its handle, means for supporting the hollow member on a supporting surface.

2. The device of claim 1, wherein the hollow member comprises a generally cylindrical first part having a slot for passage of the scalpel blade and blade-mounting shank, and a second part having a passage for the scalpel shank defining shoulder portions engaging the blade rear part, whereby pushing in of the scalpel handle causes the blade to be detached from the shank and allows removal of the handle.

3. The device of claim 2, wherein the second part is generally semi-circular and slightly offset from the slot whereby the scalpel when inserted is slightly tilted.

4. The device of claim 1, wherein the supporting means comprises a lower part having a flanged receiving area, and an upper part having a multi-sided member configured to removably engage the flanged receiving area in any of multiple positions, said upper part further having a plurality of differently-oriented receiving regions for removably receiving the hollow member.

5. The device of claim 4, wherein the multi-sided member is hexagonal.

6. A device as claimed in claim 1, wherein the supporting means comprises a base member, a plurality of upstanding members having openings and mounted on said base, said hollow member having at its bottom a wall defining a cavity sized to removably fit over and be supported on either of the upstanding members.

7. A device as claimed in claim 6, wherein the upstanding members have multi-sided configurations, the said cavity is multi-sided, and the said hollow member has a depending closed nipple.

8. The device of claim 6, wherein the multi-sided member is hexagonal.

* * * * *